United States Patent
Goraltchouk et al.

(10) Patent No.: US 8,487,012 B2
(45) Date of Patent: Jul. 16, 2013

(54) OPEN CELLED FOAMS, IMPLANTS INCLUDING THEM AND PROCESSES FOR MAKING SAME

(75) Inventors: Alexei Goraltchouk, Santa Barbara, CA (US); Jordan M. Thompson, Scotts Valley, CA (US); Dennis E. Van Epps, Goleta, CA (US)

(73) Assignee: Allergan, Inc., Irvine, CA (US)

( * ) Notice: Subject to any disclaimer, the term of this patent is extended or adjusted under 35 U.S.C. 154(b) by 204 days.

(21) Appl. No.: 13/012,991

(22) Filed: Jan. 25, 2011

(65) Prior Publication Data
US 2011/0184531 A1  Jul. 28, 2011

Related U.S. Application Data

(60) Provisional application No. 61/299,218, filed on Jan. 28, 2010.

(51) Int. Cl.
*A61F 2/12* (2006.01)

(52) U.S. Cl.
USPC ............. 521/62; 264/50; 264/46.6; 264/46.4; 264/51; 264/102; 427/2; 623/7

(58) Field of Classification Search
USPC ............................................ 521/65; 121/898
See application file for complete search history.

(56) References Cited

U.S. PATENT DOCUMENTS

| | | | |
|---|---|---|---|
| 2,805,208 A | 9/1957 | Roche | |
| 3,189,921 A | 6/1965 | Pangman | |
| 3,293,663 A | 12/1966 | Cronin | |
| 3,366,975 A | 2/1968 | Pangman | |
| 3,559,214 A | 2/1971 | Pangman | |
| 3,600,718 A | 8/1971 | Boone | |
| 3,665,520 A | 5/1972 | Perras | |
| 3,852,832 A | 12/1974 | McGhan | |
| 3,934,274 A | 1/1976 | Hartley, Jr. | |
| 4,157,085 A | 6/1979 | Austad | |
| 4,231,979 A | 11/1980 | White et al. | |
| 4,264,990 A | 5/1981 | Hamas | |
| 4,298,997 A | 11/1981 | Rybka | |

(Continued)

FOREIGN PATENT DOCUMENTS

| | | |
|---|---|---|
| EP | 0230672 | 8/1987 |
| EP | 0315814 | 5/1989 |

(Continued)

OTHER PUBLICATIONS

"International Search Report and the Written Opinion of the International Searching Authority", PCT Patent Application No. PCT/US2011/022232, mailed Sep. 8, 2011.

(Continued)

*Primary Examiner* — Randy Gulakowski
*Assistant Examiner* — Christina Wales
(74) *Attorney, Agent, or Firm* — Linda Fox; Stephen Donovan; Debra Condino

(57) ABSTRACT

Described herein are open celled foams including a matrix of interconnected spheres. Also described herein are methods of making open celled foams as well as making composite members with open celled foam coatings covering at least a portion of the composite member. The open celled foams described herein are silicone based materials and can be used to coat implants such as breast implants and function to encourage tissue ingrowth and reduce capsular formation.

9 Claims, 11 Drawing Sheets

U.S. PATENT DOCUMENTS

| | | | |
|---|---|---|---|
| 4,298,998 A | 11/1981 | Naficy | |
| 4,329,385 A | 5/1982 | Banks | |
| 4,428,082 A | 1/1984 | Naficy | |
| 4,433,440 A | 2/1984 | Cohen | |
| 4,470,160 A | 9/1984 | Cavon | |
| 4,482,577 A | 11/1984 | Goldstein | |
| 4,499,211 A | 2/1985 | Walch | |
| 4,531,244 A | 7/1985 | Hamas | |
| 4,573,999 A | 3/1986 | Netto | |
| 4,592,755 A | 6/1986 | Penton | |
| 4,610,690 A | 9/1986 | Tiffamy | |
| 4,631,296 A * | 12/1986 | Bauman et al. | 521/65 |
| 4,636,213 A | 1/1987 | Pakiam | |
| 4,643,733 A | 2/1987 | Becker | |
| 4,648,880 A | 3/1987 | Brauman | |
| 4,650,487 A | 3/1987 | Chaglassian | |
| 4,651,717 A | 3/1987 | Jakubczak | |
| 4,681,587 A | 7/1987 | Eberl | |
| 4,740,208 A | 4/1988 | Cavon | |
| 4,772,285 A | 9/1988 | Ksander | |
| 4,773,908 A | 9/1988 | Becker | |
| 4,773,909 A | 9/1988 | Chaglassian | |
| 4,790,848 A | 12/1988 | Cronin | |
| 4,795,464 A | 1/1989 | Eberl | |
| 4,803,025 A | 2/1989 | Brockmeyer | |
| 4,828,560 A | 5/1989 | Heyler | |
| 4,840,628 A | 6/1989 | Cavon | |
| 4,841,992 A | 6/1989 | Sasaki | |
| 4,859,383 A | 8/1989 | Dillon | |
| 4,859,712 A * | 8/1989 | Cox | 521/62 |
| 4,889,744 A | 12/1989 | Quaid | |
| 4,899,764 A | 2/1990 | Gauger | |
| 4,902,294 A | 2/1990 | Gosserez | |
| 4,906,423 A | 3/1990 | Frisch | |
| 4,936,858 A | 6/1990 | O'Keeffe | |
| 4,944,749 A | 7/1990 | Becker | |
| 4,944,750 A | 7/1990 | Cox, Jr. | |
| 4,950,292 A | 8/1990 | Audretsch | |
| 4,955,907 A | 9/1990 | Ledergerber | |
| 4,955,909 A | 9/1990 | Ersek | |
| 4,960,425 A | 10/1990 | Yan | |
| 4,965,430 A | 10/1990 | Curtis | |
| 4,969,899 A | 11/1990 | Cox, Jr. | |
| 5,002,572 A | 3/1991 | Picha | |
| 5,007,929 A | 4/1991 | Quaid | |
| 5,007,940 A | 4/1991 | Berg | |
| 5,022,942 A | 6/1991 | Yan | |
| 5,026,394 A | 6/1991 | Baker | |
| 5,034,422 A | 7/1991 | Triolo et al. | |
| 5,035,249 A | 7/1991 | Sasaki | |
| 5,092,348 A | 3/1992 | Dubrul | |
| 5,092,882 A | 3/1992 | Lynn | |
| 5,104,409 A | 4/1992 | Baker | |
| 5,116,387 A | 5/1992 | Berg | |
| 5,135,959 A | 8/1992 | Hill | |
| 5,146,933 A | 9/1992 | Boyd | |
| 5,147,398 A | 9/1992 | Lynn | |
| 5,158,571 A | 10/1992 | Picha | |
| 5,158,573 A | 10/1992 | Berg | |
| 5,171,269 A | 12/1992 | Bark | |
| 5,185,297 A | 2/1993 | Park | |
| 5,207,709 A | 5/1993 | Picha | |
| 5,236,453 A | 8/1993 | Picha | |
| 5,236,454 A | 8/1993 | Miller | |
| 5,236,457 A | 8/1993 | Devanathan | |
| 5,246,454 A | 9/1993 | Peterson | |
| 5,282,856 A | 2/1994 | Ledergerber | |
| 5,296,069 A | 3/1994 | Robert | |
| 5,348,788 A | 9/1994 | White | |
| 5,354,338 A | 10/1994 | Ledergerber | |
| 5,358,521 A | 10/1994 | Shane | |
| 5,376,117 A * | 12/1994 | Pinchuk et al. | 623/8 |
| 5,383,929 A | 1/1995 | Ledergerber | |
| 5,437,824 A | 8/1995 | Carlisle | |
| 5,441,919 A | 8/1995 | Park | |
| 5,447,535 A | 9/1995 | Muller | |
| 5,455,100 A | 10/1995 | White | |
| 5,480,430 A | 1/1996 | Carlisle | |
| 5,496,367 A | 3/1996 | Fisher | |
| 5,496,370 A | 3/1996 | Hamas | |
| 5,507,808 A | 4/1996 | Becker | |
| 5,522,896 A | 6/1996 | Prescott | |
| 5,525,275 A | 6/1996 | Iverson | |
| 5,534,023 A | 7/1996 | Henley | |
| 5,545,217 A | 8/1996 | Offray | |
| 5,545,220 A | 8/1996 | Andrews | |
| 5,549,671 A | 8/1996 | Waybright | |
| 5,571,179 A | 11/1996 | Manders | |
| 5,589,176 A | 12/1996 | Seare | |
| 5,605,693 A | 2/1997 | Seare | |
| 5,607,473 A | 3/1997 | Weber-Unger | |
| 5,624,674 A | 4/1997 | Seare, Jr. | |
| 5,630,843 A | 5/1997 | Rosenberg | |
| 5,630,844 A | 5/1997 | Dogan | |
| 5,653,755 A | 8/1997 | Ledergerber | |
| 5,658,330 A | 8/1997 | Carlisle et al. | |
| 5,674,285 A | 10/1997 | Quaid | |
| 5,681,572 A | 10/1997 | Seare, Jr. | |
| 5,779,734 A | 7/1998 | Ledergerber | |
| 5,798,065 A * | 8/1998 | Picha | 264/46.4 |
| 5,824,081 A | 10/1998 | Knapp | |
| 5,843,189 A | 12/1998 | Perouse | |
| 5,855,588 A | 1/1999 | Young | |
| 5,871,497 A | 2/1999 | Young | |
| 5,895,423 A | 4/1999 | Becker | |
| 5,935,164 A | 8/1999 | Iversen | |
| 5,961,552 A | 10/1999 | Iversen | |
| 5,964,803 A | 10/1999 | Iversen | |
| 5,965,076 A | 10/1999 | Banks | |
| 5,984,943 A | 11/1999 | Young | |
| 6,071,309 A | 6/2000 | Knowlton | |
| 6,074,421 A | 6/2000 | Murphy | |
| 6,083,262 A | 7/2000 | Caravel | |
| 6,099,565 A | 8/2000 | Sakura | |
| 6,113,634 A | 9/2000 | Weber-Unger | |
| 6,146,418 A | 11/2000 | Berman | |
| 6,183,514 B1 | 2/2001 | Becker | |
| 6,187,043 B1 | 2/2001 | Ledergerber | |
| 6,203,570 B1 | 3/2001 | Baeke | |
| 6,206,930 B1 | 3/2001 | Burg | |
| 6,214,045 B1 | 4/2001 | Corbitt, Jr. | |
| 6,214,926 B1 | 4/2001 | Winn | |
| 6,315,796 B1 | 11/2001 | Eaton | |
| 6,387,133 B1 | 5/2002 | Perouse | |
| 6,432,138 B1 | 8/2002 | Offray | |
| 6,464,726 B1 | 10/2002 | Heljenek | |
| 6,520,989 B1 | 2/2003 | Eaton | |
| 6,531,523 B1 | 3/2003 | Davankov et al. | |
| 6,544,287 B1 | 4/2003 | Johnson | |
| 6,596,404 B1 * | 7/2003 | Albaugh et al. | 428/447 |
| 6,602,452 B2 | 8/2003 | Schuessler | |
| 6,605,116 B2 | 8/2003 | Falcon | |
| 6,638,308 B2 | 10/2003 | Corbitt, Jr. | |
| 6,673,285 B2 | 1/2004 | Ma | |
| 6,692,527 B1 | 2/2004 | Bellin | |
| 6,755,861 B2 | 6/2004 | Nakao | |
| 6,802,861 B1 | 10/2004 | Hamas | |
| 6,811,570 B1 | 11/2004 | Gehl | |
| 6,818,673 B2 | 11/2004 | Ferguson | |
| 6,875,233 B1 | 4/2005 | Turner | |
| 6,881,226 B2 | 4/2005 | Corbitt, Jr. | |
| 6,900,055 B1 | 5/2005 | Fuller et al. | |
| 6,913,626 B2 | 7/2005 | McGhan | |
| 6,916,339 B1 | 7/2005 | Missana | |
| 6,921,418 B2 | 7/2005 | Ledergerber | |
| 6,932,840 B1 | 8/2005 | Bretz | |
| 7,081,135 B2 | 7/2006 | Smith et al. | |
| 7,081,136 B1 | 7/2006 | Becker | |
| 7,105,116 B2 | 9/2006 | Bellin | |
| 7,169,180 B2 | 1/2007 | Brennan | |
| 7,192,450 B2 | 3/2007 | Brauker et al. | |
| 7,244,270 B2 | 7/2007 | Lesh | |
| 7,323,208 B2 | 1/2008 | Ma | |
| 7,476,249 B2 | 1/2009 | Frank | |
| 7,520,896 B2 | 4/2009 | Benslimane | |
| 7,547,393 B2 | 6/2009 | Ramaswamy et al. | |
| 7,625,405 B2 | 12/2009 | Purkait | |

| | | |
|---|---|---|
| 7,632,228 B2 | 12/2009 | Brauker et al. |
| 7,632,291 B2 | 12/2009 | Stephens |
| 7,641,688 B2 | 1/2010 | Lesh |
| 7,645,475 B2 | 1/2010 | Prewett |
| 2002/0038147 A1 | 3/2002 | Miller |
| 2002/0193885 A1 | 12/2002 | Legeay |
| 2003/0036803 A1 | 2/2003 | McGhan |
| 2003/0093151 A1 | 5/2003 | Zhang |
| 2003/0105469 A1 | 6/2003 | Karmon |
| 2003/0205846 A1 | 11/2003 | Bellin |
| 2003/0208269 A1 | 11/2003 | Eaton et al. |
| 2004/0010225 A1 | 1/2004 | Schuessler |
| 2004/0115241 A1 | 6/2004 | Calhoun |
| 2004/0127985 A1 | 7/2004 | Bellin |
| 2004/0143327 A1 | 7/2004 | Ku |
| 2004/0148024 A1 | 7/2004 | Williams |
| 2004/0153151 A1 | 8/2004 | Gonzales |
| 2004/0213986 A1 | 10/2004 | Kim et al. |
| 2005/0055093 A1 | 3/2005 | Brennan |
| 2005/0070124 A1 | 3/2005 | Miller et al. |
| 2005/0122169 A1 | 6/2005 | Watanabe |
| 2005/0196452 A1 | 9/2005 | Boyan et al. |
| 2005/0216094 A1 | 9/2005 | Prewett |
| 2006/0036266 A1 | 2/2006 | Sulamanidze et al. |
| 2006/0036320 A1 | 2/2006 | Job |
| 2006/0136056 A1 | 6/2006 | Wohl |
| 2006/0224239 A1 | 10/2006 | Tiahrt |
| 2006/0229721 A1 | 10/2006 | Ku |
| 2006/0235094 A1 | 10/2006 | Habibi-Naini |
| 2006/0246121 A1 | 11/2006 | Ma et al. |
| 2007/0093911 A1 | 4/2007 | Fricke |
| 2007/0104693 A1 | 5/2007 | Quijano |
| 2007/0104695 A1 | 5/2007 | Quijano |
| 2007/0116735 A1 | 5/2007 | Calhoun |
| 2007/0135916 A1 | 6/2007 | Maxwell |
| 2007/0154525 A1 | 7/2007 | Calhoun |
| 2007/0190108 A1 | 8/2007 | Datta et al. |
| 2007/0198085 A1 | 8/2007 | Benslimane |
| 2008/0009830 A1 | 1/2008 | Fujimoto et al. |
| 2008/0071371 A1 | 3/2008 | Elshout |
| 2008/0075752 A1 * | 3/2008 | Ratner et al. ............... 424/426 |
| 2008/0154366 A1 | 6/2008 | Frank |
| 2008/0241212 A1 | 10/2008 | Moses |
| 2008/0268019 A1 | 10/2008 | Badylak et al. |
| 2008/0312739 A1 | 12/2008 | Agerup |
| 2009/0045166 A1 | 2/2009 | Li |
| 2009/0082864 A1 | 3/2009 | Chen |
| 2009/0087641 A1 | 4/2009 | Favis et al. |
| 2009/0093878 A1 | 4/2009 | Glicksman |
| 2009/0118829 A1 | 5/2009 | Powell |
| 2009/0125107 A1 | 5/2009 | Maxwell |
| 2009/0169716 A1 | 7/2009 | Linhardt |
| 2009/0198331 A1 | 8/2009 | Kesten et al. |
| 2009/0198332 A1 | 8/2009 | Becker |
| 2009/0198333 A1 | 8/2009 | Becker |
| 2010/0042211 A1 | 2/2010 | Van Epps et al. |
| 2011/0035004 A1 | 2/2011 | Maxwell |

FOREIGN PATENT DOCUMENTS

| | | |
|---|---|---|
| EP | 0522585 | 1/1993 |
| EP | 0522585 A1 * | 1/1993 |
| EP | 1532942 | 5/2005 |
| FR | 2840617 A1 * | 12/2003 |
| JP | 2003-062062 | 4/2003 |
| JP | 2007-029717 | 8/2007 |
| WO | WO 98/10803 | 3/1998 |
| WO | WO 00/24437 | 5/2000 |
| WO | WO 2004/037318 | 5/2004 |
| WO | WO 2004/062531 | 7/2004 |
| WO | WO 2006/133366 | 12/2006 |
| WO | WO 2009/061672 | 5/2009 |
| WO | WO 2009/110917 | 9/2009 |
| WO | WO 2011/094155 | 8/2011 |
| WO | WO 2011/097499 | 8/2011 |

OTHER PUBLICATIONS

Alvarez et al, "Synthesis of Macro/Mesoporous Silica and Carbon Monoliths by Using a Commercial Polyurethane Foam as Sacrificial Template", Materials Letters, 61, 2378-2381 (2007).

Barnsley et al., "Textured Surface Breast Implants in the Prevention of Capsular Contracture Among Breast Augmentation Patients: A Meta-Analysis of Randomized Controlled Trials", Plastic and Reconstructuve Surgery, 2006, 117(7), 2182-2190.

Barr et al., "Current Implant Surface Technoogy: An Examination of Their Nanostructure and Their Influence on Fibroblas Alignment and Biocompatibility", Elastic, 2008, 9, 198-217.

Brauker et al., "Neovascularization of synthetic membranes directed by membrane microarchitecture", Journal of Biomedical Materials Research, 1995, pp. 1517-1524, vol. 29, John Wiley & Sons, Inc.

Brohim et al., "Early Tissue Reaction to Textured Breast Implant Surfaces", Anals of Plastic Surgery, 28(4): 354-362, 1992.

Inamed Aesthetics Brochure, Directions for Use Style 410 Silicone-Filled Breast Implants (2003).

Ma, "Scaffolds for tissue fabrications", Materials Today, 2004, 7, 30-40.

Mikos et al., "Formation of Highly Porous Biodegradable Scaffolds for Tissue Engineeing", Electronic Journal of Biotechnology, 2000, 3(2), 114-119.

Minami et al., "The composition and behavior of capsules around smooth and textured breast implants in pigs", Plastic and Reconstructive Surgery, 2006, 118940, 874-884.

Murphy et al. "Salt Fusion: An Approach to Improve Pore Interconnectivity within Tissue Engineering Scaffolds", Tissue Engineering, vol. 8, No. 1, 2002, pp. 43-52 (XP-002588127).

Sharkawy et al. "Engineering the tissue which encapsulates subcutaneous implants", II. Plasma-tissue exchange properties, 1998, pp. 586-597, John Wiley & Sons, Inc.

Wei et al., "Macroporous and Nanofibers Polymer Scaffolds and Polymer/Bone-Like Apatite Composite Scaffolds Generated by Sugar Spheres", Journal of Biomedical Materials Research Part A, 2006, 306-315.

Zhang et al., "Macroporous Alumina Monoliths Prepared by Filling Polymer Foams with Alumina Hydrosols", J. Mater Sci., 44, 931-938 (2009).

* cited by examiner

OPEN CELLED FOAMS, IMPLANTS INCLUDING THEM AND PROCESSES FOR MAKING SAME

RELATED APPLICATION

This application claims priority to U.S. Provisional Patent Application No. 61/299,218, filed on Jan. 28, 2010, the entire disclosure of which is incorporated herein by this specific reference.

FIELD OF THE INVENTION

The present invention relates to open celled foams and methods for making and use of same.

BACKGROUND

Whether for cosmetic, aesthetic, or reconstructive purposes, soft tissue implants have become commonplace in today's society. Despite their growing popularity, a soft tissue implant can result, in some cases, in capsular contracture. Soon after an implant is placed into the body an inflammatory response begins to deposit collagen around the implant in the form of a fibrous capsule. In most cases for larger smooth implants the fibrous capsule is comprised of highly aligned and organized collagen fibers. As the fibrous capsule matures, certain events may trigger the differentiation of fibroblasts to a contractile phenotype, for example, myofibroblasts, and if the collagen fibers adjacent to the implant are aligned, capsular contracture ensues.

Capsular contracture can be debilitating to a patient because of discomfort or even pain, and can diminish the efficacy of the cosmetic or aesthetic results in both the look and feel of the implant.

Problems with capsular formation and contracture occur in many implant types such as pacemakers, dura mater substitutes, implantable cardiac defibrillators as well as breast and other esthetic implants. Implants with smooth surfaces in particular suffer most from capsular formation and contracture. Surface texturing has been shown to reduce capsular contracture when compared to common smooth surface implants when the implant is placed subglandularly.

Polyurethane textured coatings have been developed in an effort to reduce capsular formation and contracture. However, these coatings are biodegradable, and will therefore, lose any potential efficacy once the polyurethanes degrade. Also, some types of polyurethanes have been shown to degrade to potentially carcinogenic byproducts in vitro. Even further still, the manufacturing of polyurethane foam coated implants is increasingly complicated raising the cost of the resulting implant.

As such, there is a need in the art for textured implant coatings that reduce or even eliminate capsular formation and contracture. The present description fulfills this need in the art by providing coatings, implants including the coatings and methods of making and using the same.

SUMMARY

Described herein are open celled foams including matrices of interconnected spheres. Also described herein are methods of making open celled foams as well as methods of making composite members with open celled foam coatings covering at least a portion of the composite member's surface. Methods of using these foams are also described.

In one embodiment, the spheres comprise substantially pure silicone and have a diameter of between about 10 µm and about 2,000 µm or about 25 µm and about 200 µm. The matrix of interconnected spheres can have a theoretical void space of about 50% to about 99%. In other embodiments, the theoretical void space is between about 60% and 88%. The matrix of interconnected spheres can have a physical void space of about 50% to about 70%. The silicone used to make the foams can be, for example, a room temperature vulcanizing (RTV) silicone or high temperature vulcanizing (HTV) silicone.

Further, in one embodiment, soft tissue implants are described comprising a textured coating on at least a portion of the soft tissue implant, the coating comprising a matrix of interconnected spheres, the spheres comprising substantially pure silicone wherein the matrix of interconnected spheres has a theoretical void space of about 50% to about 99%. In another embodiment, the implant is a breast implant. In other embodiments, the implant can be a pace maker lead, a medical port, catheter, dura mater substitutes, hernia meshes or the like.

In one embodiment described herein are processes for forming open celled foams comprising the steps of: combining a first composition comprising a first organic solvent and at least one extractable agent, and a second composition comprising a second organic solvent and at least one silicone matrix agent thereby forming a mixture, wherein the at least one matrix agent is less than about 40% v/v of the mixture; agitating the mixture thereby forming an emulsion; and curing the emulsion thereby forming the open celled foam, wherein the matrix open celled foam has a theoretical void space of about 50% to about 99%.

In another embodiment, the first organic solvent and the second organic solvent are the same or different and are selected from the group consisting of dichloromethane, water, xylene, acetone, methanol, methyl acetate, hexane, benzene toluene, isopropyl alcohol, or other suitable protic or aprotic solvent. In still another embodiment, curing step further comprises heating the emulsion. In some embodiments, the process further comprises the step of casting the emulsion before the curing step, in other embodiments the emulsion may be used in any other conventional coating process, such as curtain coating, spray coating, dip coating, or the like.

In another example embodiment, the removable polymer is selected from group consisting of polyethylene glycol, poly propylene glycol, poly acrylic acid, poly acrylamide, dextran, chitosan, alginate, carboxymethyl cellulose, hydroxypropyl cellulose, polyvinyl alcohol, polyvinyl pyrrolidone, or other aliphatic or aromatic polymers, co-polymers thereof, blends thereof or combinations thereof. A removable polymer, can be soluble, or sublimable or degradable or a combination thereof, wherein the processing thereof does not substantially affect the silicone matrix). disposed in the hub, further prevents detachment of the hub from the syringe distal end during ejection of the viscous fluid.

In other embodiments, the process further comprises the step of dipping a soft tissue implant into the emulsion before the curing step. The soft tissue implant can be, for example, a breast implant. In other embodiments, the implant can be a pace maker lead, a medical port, catheter, dura mater substitutes, hernia meshes or the like.

In one embodiment described herein are implantable composite members having an external surface at least a portion of which is covered by an open celled foam structure, the member made by the method comprising the steps of: (a) providing an implantable shell; (b) providing an open celled foam comprising a matrix of interconnected spheres, the spheres comprising substantially pure silicone, and wherein the matrix of interconnected spheres has a theoretical void space of about 50% to about 99%; (c) applying a bonding substance to the open celled foam thereby forming a bondable open celled foam; (d) applying the bondable open celled foam to at least a portion of the implantable shell; (e) curing the bonding substance; and (f) forming a composite material having an external surface at least a portion of which is covered by an open celled foam. Alternatively the bonding substance can be applied to the device upon which the open cell foam will be laminated.

In another embodiment, the implantable shell is a breast implant. In still other embodiments, the curing step further comprises heating the emulsion.

Further described herein are composite materials useful as a shell for a prosthesis having a surface as illustrated in any one of FIG. 9, FIG. 10, FIG. 11, FIG. 12, FIG. 13, FIG. 14, FIG. 15, FIG. 16, FIG. 17 or FIG. 18.

DETAILED DESCRIPTION

Figure 1:
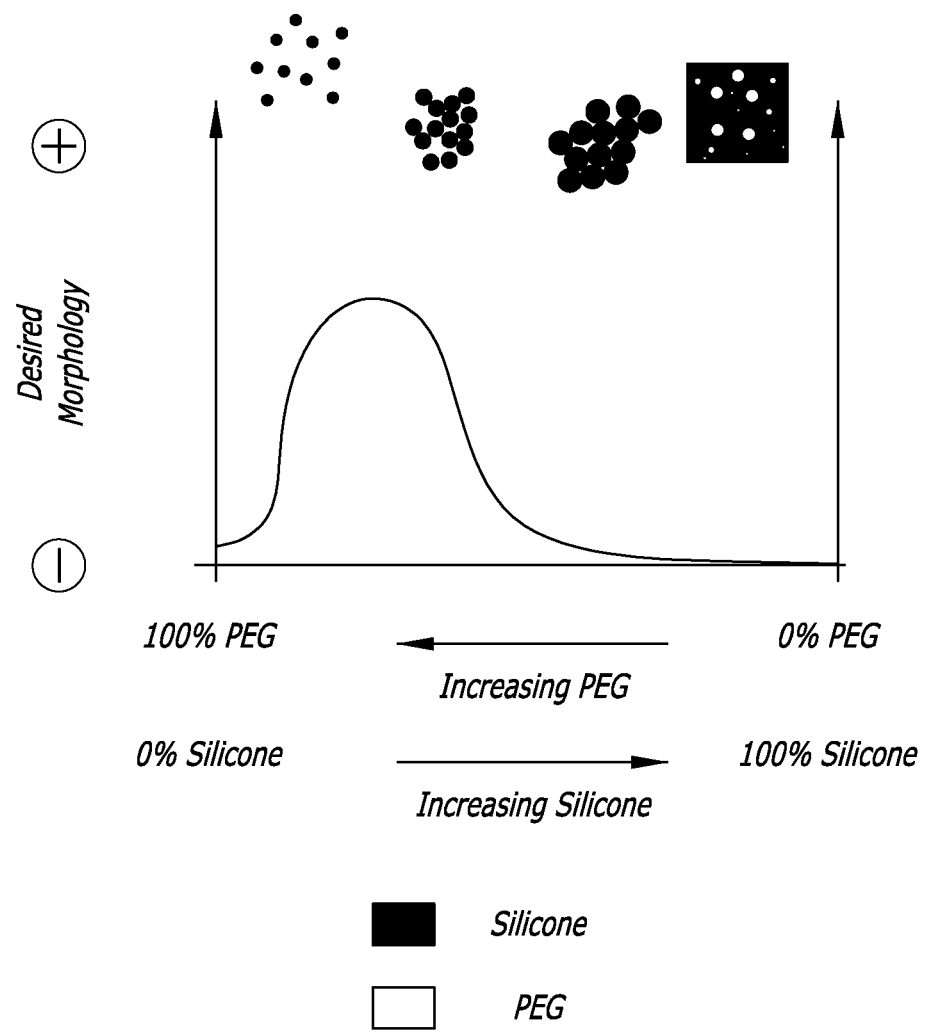
FIG. 1 illustrates an exemplary binary phase diagram for open celled foams as described herein.

Described herein are open celled foams including matrices of interconnected spheres. Also described herein are methods of making open celled foams as well as making composite members with open celled foam coatings covering at least a portion of the composite member's surface.

The foams described herein can be coated on a composite member such as an implant. The implant can be a soft tissue implant, an artificial bone, a joint implant, a bone screw, an implantable medical device, or a combination thereof. In one embodiment, the soft tissue implant is selected from breast implants, cheek implants, buttocks implants, lip implants and other facial implants. Implantable medical devices can be coated, at least partially, with the open celled foams described herein. The implantable medical devices can include, but are not limited to, pacemaker leads, stents, stent grafts, implantable pumps, implantable pump systems, gastric band devices, access ports, heart valves, implantable tubing, and the like. The implant can in some embodiments be any implant that is located adjacent to muscle tissue.

The opened celled foams themselves can be formed of substantially pure silicone and generally comprise a highly interconnected matrix of spheres. For example, the "substantially pure" foams can include greater than about 50% silicone, greater than about 75% silicone, greater than about 90% silicone, greater than about 95% silicone or greater than about 99% silicone. The remaining component can be comprised of fused silica, other elastomers, thermoplastics or thermosets, ceramics metals, metal alloys or composites thereof.

In some embodiments, a portion of the spheres are hollow. For example, less than about 1% of the spheres are hollow, less than about 5% of the spheres are hollow, less than about 10% of the spheres are hollow or less than about 25% of the spheres are hollow. The percentage of hollow spheres will be dependent on the processes used to make the open celled foam.

The matrix of interconnected spheres making up the open celled foams described herein can have an associated void space within them. A theoretical void space can be a calculated void space that is dependent on the composition of the spheres themselves and the leachable agent, for example. Theoretical void space is a term of art that is well understood by those of skill in the art, and in the context of the present disclosure can be generally defined as the percentage by volume of the foam occupied by the leachable agent on a dry basis. The theoretical void space can be greater than about 50% of the foam, greater than about 75% of the foam greater than about 90% of the foam, greater than about 95% of the foam or greater than about 99% of the foams. In some embodiments, the theoretical void space can be about 50% to about 99% of the foam or about 60% to about 88% of the foams.

Once the open celled foams have been cured and leachable agents removed, the foams have a characteristic actual or physical void space between the matrix of interconnected microspheres. This physical void space can be greater than about 30%, greater than about 40%, greater than about 50%, greater than about 60% or even as much as 70%. Ranges of both theoretical and physical void space including the percentages described are within the scope of the present description.

Tissue ingrowth occurs into the voids within the foam when the open celled foams described herein are used to coat an implantable medical device, such as a soft tissue implant. The ingrowth of tissue is intended to promote the disorganization of collagen fibers, but may be used to increase the surface area of the implant-tissue interface for example for potential drug delivery, increased cellular proliferation (e.g. tissue bulking) or any other application.

The physical void space of the open celled foams described herein may, in some embodiments, be different than the theoretical void space. In practice, starting with a theoretical void space, may not translate into an actual void space because of factors such as phase separation, settling effects, solvent evaporation, capsule formation in the silicone in place of spheres, and the like.

The silicone used to form the open celled foams, also termed the matrix agent, can be any biocompatible silicone known in the art. The matrix agent can be a RTV silicone, HTV silicone, an acetoxy, oxime or platinum curing system or other silicone system. In one embodiment, the silicone is room temperature vulcanizing (RTV) silicone. In another embodiment, the silicone is high temperature vulcanizing (HTV) silicone.

The interconnected spheres making up the matrix of the foams described herein have diameters between about 10 µm and about 2,000 µm, between about 1 µm and about 500 µm, between about 10 µm and about 250 µm, between about 25 µm and about 200 µm, or between about 50 µm and about 100 µm.

In one embodiment, open celled foams described herein can be formed by an emulsion process. The process involves combining two compositions in the form of solutions, mixtures, suspensions or emulsions. In one embodiment, two solutions are used. The first composition (composition 1) contains one or more solvents and one or more extractable agents. The second composition (composition 2) contains one or more solvents and one or more matrix agents. The ratio of the composition 1:2 can be varied to obtain the optimal results; the total dissolved solids in each composition may be varied to obtain the optimal results, and the starting component temperatures can be varied to obtain optimal results.

The compositions are then combined, agitated to produce an emulsion or mixture and cast or injected into flat moulds for curing. It will be appreciated by those skilled in the art that the materials in their emulsified form can be used in any end processing application that can be envisioned by a person skilled in the art of coating, lamination or general material or device fabrication. Heat can be optionally applied to the system for curing, or the system may be left to dry at room temperature. Further, the system can be subjected to a vacuum prior to the application of heat. After the removal of the leachable agent(s) by heat and/or vacuum and/or dissolution and/or sublimation, the resulting matrix material is considered cured. If the resulting matrix material cannot maintain its shape without the leachable agent(s), the curing can happen during or before the removal of the leachable agent. The resulting product is an open celled foam.

The emulsion process can be considered a phase inversion process because the two compositions are mixed in a manner which creates a phase inverted emulsion (with respect to a continuous phase of silicone) wherein the silicone phase is in the spherical shape and the leachable phase in the continuous shape. Without wishing to be bound by any particular theory, it is believed that because silicone oils have very low surface tension (high cohesivity in liquid form), it is necessary to decrease the silicone content in the final solution mix in order to create the phase inversion. As the phase inversion occurs, the silicone is in the sphere form and the leachable portion is in the matrix form. However, because of the low surface tension of silicone and its unique ability to readily wet surfaces (as well as high cohesivity), as the emulsion dries and cures, the resulting silicone microspheres become attached to one another thereby forming a network of interconnected spheres. The final form of the material is a solid sheet with a microsphere matrix microstructure.

A surprising feature of the open celled foams described herein is the ratio of total solids. The silicone is in the minority phase compared to the leachable phase. As a result of silicone and its corresponding oils having very low surface tensions, on the order of 21.5 mN/m for a >300 cst fluid, they are very prone to readily wet clean surfaces (for comparative purposes water is 71.97 mN/m at 25° C.). Silicones ability to fully wet most surfaces prevents the use of standard porogens (such as salt sugar or standard emulsions) as matrices for creating a structure that is open enough to be biocompatible and sufficiently open to disorganize the surrounding tissues for the application of preventing or reducing the frequency of capsular contracture. The present open celled foams utilize phase inversion of the emulsion to create interconnections. It has been observed that until phase inversion of the emulsion occurs, the cells of the final foam remain closed. Furthermore, if the emulsion is too dilute, the material falls apart as microspheres. A surprising result of the present foams is that the material falls apart at much lower concentrations of total dissolved solids and matrix/leachable v/v ratios as compared to most conventional materials prepared using this method.

The highly interconnected soft structure of the opened celled foams described herein creates the optimal geometry for preventing classical capsular formation around a soft tissue implant. For example, one can construct a set of binary phase diagram with a two component system for each particular configuration of solvent ratios. In such a system, as illustrated in FIG. 1, a desired range can be selected where the matrix agent, or non-leachable component, forms microspheres which are adherent to each other and thereby form a stable structure when the leachable component or agent is extracted. At concentrations of a leachable agent which exceed the desired concentration the material will fall apart as microspheres after the leachable agent is extracted. Conversely, at concentrations where the leachable agent is at lower than desired concentrations a closed cell foam will be created. An individual skilled in the art can envisage such phase diagrams for different materials with appropriate surface tension properties.

In one embodiment described herein are implantable composite members having an external surface at least a portion of which is covered by an open celled foam as described herein. The implantable composite members are made by first providing an implantable shell and providing an open celled foam comprising a matrix of interconnected spheres, the spheres comprising substantially pure silicone, and wherein the matrix of interconnected spheres has a void space of about 50% to about 99%. Next, a bonding substance is applied to the open celled foam thereby forming a bondable open celled foam. The bonding substance will act as a means for attaching the open celled foam to the implantable shell. The bondable open celled foam is then applied to at least a portion of the implantable shell and the bonding substance is cured. Alternatively the bonding agent can be applied directly to the device, and not to the open celled foam. The curing of the bonding substance adheres the open celled foam to the implantable shell thereby forming a composite material having an external surface at least a portion of which is covered by an open celled foam.

In some embodiments, the bonding substance is room temperature vulcanizing silicone (RTV) or high temperature vulcanizing (HTV) silicone. The bonding substance can be applied to the open celled foams using any method known in the art, for example, brushing, spraying, dipping, curtain coating, vapor deposition methods can be used, casting methods can be used, injection molding and the like. The bonding substance can be cured using heat or any other means of aiding in curing known in the art.

After the open celled foam has been adhered to the surface of the implantable shell, extra portions of foam can be trimmed off to make a relatively smooth edge. In some embodiments, the process is termed lamination.

Open celled foams as described herein can be laminated onto a smooth implant shell using silicone adhesive. The lamination step can be done while the implant is still on the mandrel or on finished implant. The lamination process can utilize a two piece cavity in which a finished smooth implant is pressed between two open celled silicone foam sheets.

For example, the foams can be laminated onto finished smooth implants. A dispersion of HTV silicone is used as the adhesive between the implant and the foam sheets. In the process, the first foam sheet is coated with a thin layer of HTV silicone and then placed in the bottom cavity. The smooth implant is then placed on top of the foam sheet in the cavity. The second foam sheet is coated with a thin layer of HTV silicone and applied on top of the smooth implant. The top piece of the cavity is then fixed in place pressing the two foam sheets together creating a uniform interface. The silicone adhesive is allowed to cure and then the excess foam is cut off creating a uniform seam around the implant.

Another exemplary process involves laminating the foam onto a smooth implant still on a mandrel. In this process a HTV silicone is used as the adhesive between the implant and the foam sheets. The first foam sheet is coated with a thin layer of HTV silicone and then draped over the smooth implant on the mandrel in such a way that there are no wrinkles on the top surface. After this has cured, another coating of HTV silicone is applied and the foam is stretched up to cover part of the back of the implant. The smooth implant is then taken off the mandrel and the excess foam is removed. A smaller circle is cut out of a foam sheet to fit the back of the implant. A thin layer of HTV silicone is applied to the small circle of foam and the circle is attached and allowed to cure.

In another embodiment, a bonding surface is applied to the implant by dipping the implant into HTV silicone and then lamination of the foam onto the implant. The HTV silicone can be applied to the implant using any technique known to those skilled in the art, for example, by spraying curtain coating, and the like.

In yet another embodiment, the implantable shell is coated with an emulsion including an agitated mixture of a first organic solvent and at least one extractable agent, and a second organic solvent and at least one silicone matrix agent. The emulsion can also be applied to the implantable shell. A common method used to coat an implantable shell is to first form the shell itself on a mandrel using a dipping technique and then after the shell is formed, to dip that formed shell into a composition as described herein. The emulsion is then allowed to cure on the implantable shell thereby forming the open celled foam. Extractable materials can then be removed from the open celled foam using various drying and/or leaching techniques known in the art. In one example embodiment, the curing step optionally includes heating.

If the open celled foam is formed on the implantable shell itself, the step of coating and/or applying the emulsion to the implantable shell is accomplished using any method known in the art. For example, spraying, dipping, vapor deposition, brushing, and the like can be used. In an exemplary embodiment, the implantable shell is dipped into an agitated emulsion.

In some embodiments, the open celled foams can be applied only to portions of the implantable shell. For example, only the front of the shell is be coated, or only the back of the shell is be coated, or only about 20%, about 30%, about 40%, about 50%, about 60%, about 70% about 80% or about 90% of the shell is coated. In other embodiments, substantially all of the shell is coated.

In one embodiment, the implantable shell is a silicone based shell suitable for use in the manufacture of breast prosthesis or other composite members. The breast prosthesis can be any breast implant known in the art. After applying an open celled foam to a breast prosthesis as described herein, the steps required to make a finished prosthesis may be conventional. First, the opening left by the supporting mandrel is patched with uncured silicone elastomer sheeting. If the prosthesis is to be filled with silicone gel, this gel is added and cured, the filled prosthesis packaged, and the packaged prosthesis sterilized. If the prosthesis is to be inflated with a saline solution, a valve is assembled and installed, the prosthesis is post cured if required, and the prosthesis is then cleaned, packaged and sterilized. A combination silicone/saline mammary prosthesis can also be made.

In other embodiments, the implant can be a pace maker lead, a medical port catheter, dura mater substitutes, hernia meshes or the like.

The extractable agent, or removable polymer may be, for example, a water soluble material dispersed throughout the curable elastomer. Typical extractable agents or leachable materials may comprise, for example, polyethylene glycol (PEG, also known as polyoxyethylene), polyalkylene oxides including polyethylene oxide and polyethylene oxide/polypropylene oxide copolymers (also known as poloxamers), polyhydroxyethylmethacrylate, polyvinylpyrrolidone, polyacrylamide, or other substituted polyolefins and their copolymers, polylactides, polyglycolides, or other polyesters, polyanhydrides, polyorthoesters and their copolymers, proteins including albumin, peptides, liposomes, cationic lipids, ionic or nonionic detergents, salts including potassium chloride, sodium chloride and calcium chloride, sugars including galactose, glucose and sucrose, polysaccharides including soluble celluloses, heparin, cyclodextrins and dextran, and blends of the same.

When an extractable agent such as PEG is used, the molecular weight of the PEG can be influential on the way the emulsion forms. For example, in one embodiment, the PEG (monomethyl) polymer has a molecular weight of about 2,000 Da. In another embodiment, the PEG polymer has a molecular weight greater than about 750 Da. In some embodiments, the PEG molecular weight ranges from about 1,000 Da to about 100,000,000 Da, or more preferably about 1,000 Da to about 10,000 Da.

In some embodiments, the extractable agent is an agent selected from the group of agents consisting of polyvinyl alcohol, polyethylene glycol, polyethylene oxide, polyacrylic acid; polymethacrylate, poly-lactide, polyglycolide, polycaprolactone, polydioxanone, derivatives thereof, blends thereof, copolymers thereof, terpolymers thereof, and combinations thereof or other biodegradable or non-biodegradable polymers, metals ceramics, composites, or combinations thereof.

The solvent component of the composition can include a solvent selected from the group consisting of xylene, pentane, hexane, dichloromethane (DCM), dimethyl sulfoxide, dioxane, NMP, DMAc, and combinations thereof or any other protic or aprotic solvent or combinations thereof.

The presently described open celled foams comprising matrices of interconnected spheres provide soft tissue implants with the ability for tissue ingrowth into the voids within the foams once implanted. This tissue ingrowth prevents or substantially prevents the formation of a capsule around the soft tissue implant. Hence, contracture of a capsule formed around a soft tissue implant and associated bleeding is avoided using the open celled foams described herein. Thus, implants comprising the open celled foams described herein may provide relief from contracture pain from capsules surrounding the implants.

A method has been described for creating a foam outer layer having an open-cell structure on, for example, a silicone member. Further, the method can be applied to create a medical implant with an external surface layer of silicone foam having an open-cell structure for use in creating strips having a textured surface for control of scar formation, or to improve a process for making mammary prostheses. The product made by this method has utility in preventing capsular contraction, in preventing or controlling scar formation, and in anchoring medical implants.

Scar tissue formation in the healing of a wound or surgical incision is also a process involving the growth of fibrous tissue. A visible scar results from this healing process because the fibrous tissue is aligned in one direction. However, it is often aesthetically desirable to prevent or significantly reduce classical scar formation, especially in certain types of plastic surgery. A member having an open-cell structure surface made in accordance with the present invention can be placed subcutaneously within a healing wound or incision to prevent the fibrous tissue from aligning and thereby prevent or reduce scar formation.

Even further, it is often important to anchor medical implants to prevent their movement, displacement or rotation. Mammary prostheses are one example of implants that are preferentially anchored. Facial implants are another example of implants that can be anchored. With facial implants, for example, it is important that they be anchored securely against movement because of their prominent location. Providing such implants with an open-cell structure surface made in accordance with the present description is an advantageous way to ensure that they will be anchored securely as tissue ingrowth once implanted will prevent their migration.

Example 1

Formulation of Open Celled Foams

Table 1 tabulates data for open celled foams prepared according to the methods of the present description. The open celled foams are created as sheets. The formulation components and targets for optimization were total dissolved solids (TDS) in the matrix agent and in the extractable agent solution. TDS upon mixing (e.g. in the emulsion phase), which is highly correlated to viscosity, is important in stabilizing the emulsion. If the TDS are too low, the emulsion is unstable or the micro-geometrically to fine. If the TDS are too high, the emulsion cannot be created without extremely vigorous agitation and/or the micro-geometry is too coarse. Viscosity has its own implications in coating, casting and the like which are known to those skilled in the art. Also important are the ratio of solution 1 to solution 2 and the ratio of the matrix and extractable agents once in solid form. The former is important for affecting surface tension between the phases for proper microstructure formation in the emulsion process, the latter is important for creating the open celled foam structure. This ratio also plays a key role in phase separation of the emulsion.

TABLE 1

| Name | Extractable Agent | Matrix Agent | Solvent A/Solvent B | Ratio | Theoretical Void Space | Total Dissolved Solvents (%) |
|---|---|---|---|---|---|---|
| F8 | 40% PEG | 40% RTV | DCM/Xylene | 1:2 | 33.33 | 40 |
| F28 | 40% PEG | 40% RTV | DCM/Xylene | 1:1 | 50 | 40 |
| F30 | 40% PEG | 40% RTV | DCM/Xylene | 3:2 | 60 | 40 |
| F31 | 40% PEG | 40% RTV | DCM/Xylene | 2:1 | 66.67 | 40 |
| F33 | 40% PEG | 40% RTV | DCM/Xylene | 3:1 | 75 | 40 |
| F34 | 40% PEG | 40% RTV | DCM/Xylene | 4:1 | 80 | 40 |
| F35 | 60% PEG | 40% RTV | DCM/Xylene | 1:1 | 60 | 50 |
| F36 | 60% PEG | 40% RTV | DCM/Xylene | 2:1 | 75 | 53.33 |
| F38 | 40% PEG | 30% RTV | DCM/Xylene | 2:1 | 72.72 | 36.67 |
| F39 | 60% PEG | 30% RTV | DCM/Xylene | 1:1 | 66.67 | 45 |
| F40 | 60% PEG | 30% RTV | DCM/Xylene | 2:1 | 80 | 50 |
| F41 | 60% PEG | 40% RTV | DCM/Xylene | 3:1 | 81.81 | 55 |
| F42 | 60% PEG | 25% RTV | DCM/Xylene | 3:1 | 87.80 | 51.25 |
| F43 | 60% PEG | 25% RTV | DCM/Xylene | 4:1 | 90.56 | 53 |
| FPV4 | 4% PVA | 25% RTV | $H_2O$/Xylene | 1:1 | 13.8 | 14.5 |
| FPV5 | 4% PVA | 25% RTV | $H_2O$/Xylene | 2:1 | 24.24 | 11 |
| FPV6 | 4% PVA | 25% RTV | $H_2O$/Xylene | 1:2 | 7.41 | 18 |

TABLE 1-continued

| Name | Extractable Agent | Matrix Agent | Solvent A/Solvent B | Ratio | Theoretical Void Space | Total Dissolved Solvents (%) |
|---|---|---|---|---|---|---|
| FPV7 | 6% PVA | 25% RTV | H$_2$O/Xylene | 1:1 | 19.35 | 15.50 |
| FPV8 | 6% PVA | 25% RTV | H$_2$O/Xylene | 2:1 | 32.43 | 12.33 |
| FPV9 | 6% PVA | 25% RTV | H$_2$O/Xylene | 1:2 | 10.71 | 18.67 |
| FPV12 | 2% PVA | 40% RTV | H$_2$O/Xylene | 1:2 | 2.44 | 27.33 |
| FPV13 | 4% PVA | 40% RTV | H$_2$O/Xylene | 1:1 | 9.09 | 22 |
| FPV15 | 4% PVA | 40% RTV | H$_2$O/Xylene | 1:2 | 4.76 | 28.00 |
| FPV16 | 6% PVA | 40% RTV | H$_2$O/Xylene | 1:1 | 13.04 | 23 |
| FPV18 | 6% PVA | 40% RTV | H$_2$O/Xylene | 1:2 | 6.98 | 28.67 |
| FPVA4 | 4% PVA | 25% RTV | H$_2$O/DCM | 1:1 | 13.79 | 14.50 |
| FPVA7 | 6% PVA | 25% RTV | H$_2$O/DCM | 1:1 | 19.35 | 15.5 |

Example 2

Formation of an Open Celled Foam

Foam F35 from Table 1 has a theoretical void space of 60% and is prepared using a 1:1 ratio of 60% polyethylene glycol monomethyl ether (PEG) by weight in dichloromethane and 40% MED-1037 adhesive silicone by weight in xylene. The silicone and PEG dispersions are mixed at equal volumes and vigorously shaken by hand for 30 seconds. They are then immediately poured into the desired mold. The volume prepared for casting is varied depending on the size of the mold to obtain foams of varying thicknesses. A standard preparation of this formulation would be 200 mL into a 415 cm$^2$ circular mold to produce a 2 mm thick foam.

Example 3

Formation of an Additional Open Celled Foam

Foam F41 from Table 1 has a theoretical void space of 81.81% and is prepared using a 3:1 ratio of 60% PEG by weight in dichloromethane and 40% MED-1037 adhesive silicone by weight in xylene. The silicone and PEG dispersions are mixed at the ratio of 3 parts PEG to 1 part silicone and vigorously shaken by hand for 30 seconds. They are then immediately poured into the desired mold. A standard preparation of this formulation would be 200 mL into a 415 cm$^2$ circular mold to produce a 2 mm foam.

Example 4

Formation of an Additional Open Celled Foam

Foam F42 from Table 1 has a theoretical void space of 87.8% and is prepared using a 1:1 ratio of 60% PEG by weight in dichloromethane and 25% MED-1037 adhesive silicone by weight in xylene. The silicone and PEG dispersions are mixed at the ratio of 3 parts PEG to 1 part silicone and vigorously shaken by hand for 30 seconds. They are then immediately poured into the desired mold. A standard preparation of this formulation would be 400 mL into a 415 cm$^2$ circular mold to produce a 2 mm foam.

Example 5

Histological Studies

Figure 2:
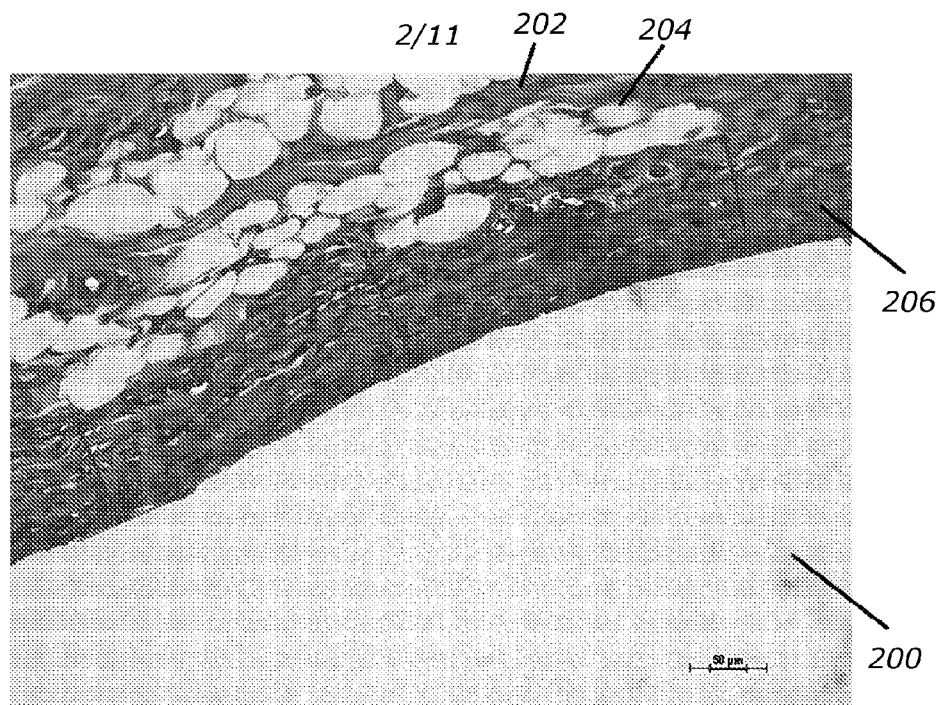
FIG. 2 illustrates a smooth implant with a formed capsule.

A smooth disk-shaped implant without a coating is implanted in a rat. FIG. 2 illustrates a typical capsule formed after implantation of smooth disk 200. At the top left corner of FIG. 2, a small amount of disorganized fascia 202 is identifiable, separated by white blobs 204 which are fat cells. Right below the fat cells, is located organized foreign body capsule 206 (organized meaning that the collagen fibers are well aligned with the biomaterial plane at the bottom right half of FIG. 2).

Figure 3:
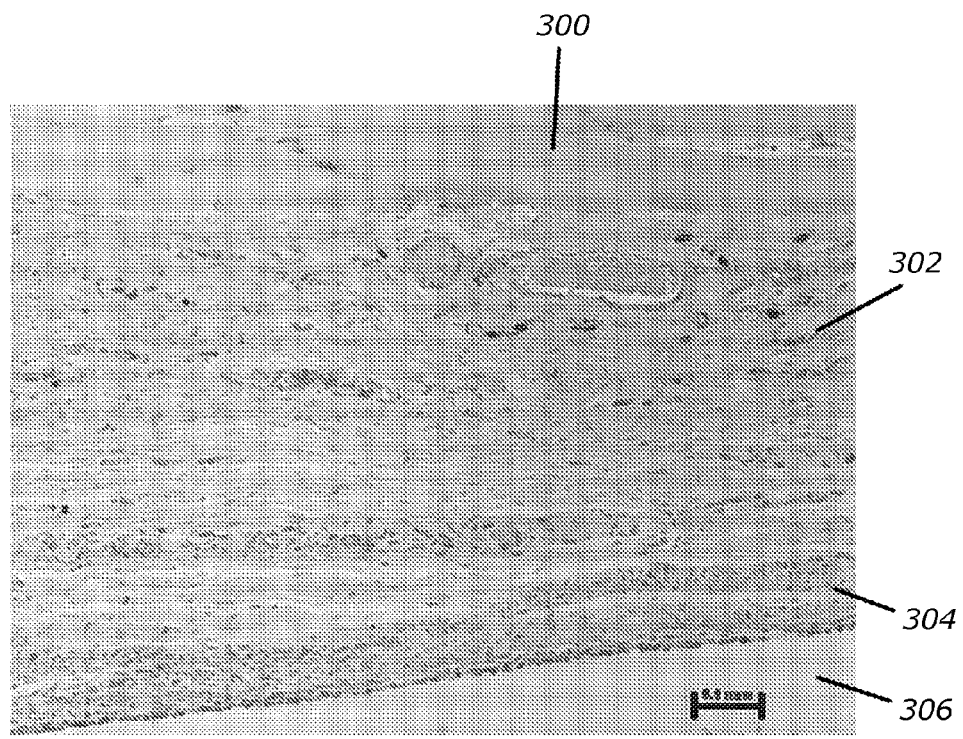
FIG. 3 illustrates another smooth implant with a formed capsule after 1.5 months in a rat.

In another example, a smooth implant without a coating at 6 weeks (1.5 months) in rat is illustrated in FIG. 3. Clearly visible is panniculus carnosus muscle top 300, followed by loose disorganized connective tissue 302 (nonpathological) followed by organized foreign body capsule 304 and smooth implant 306. Organized foreign body capsule 304 completely surrounds smooth implant 306.

Figure 4:
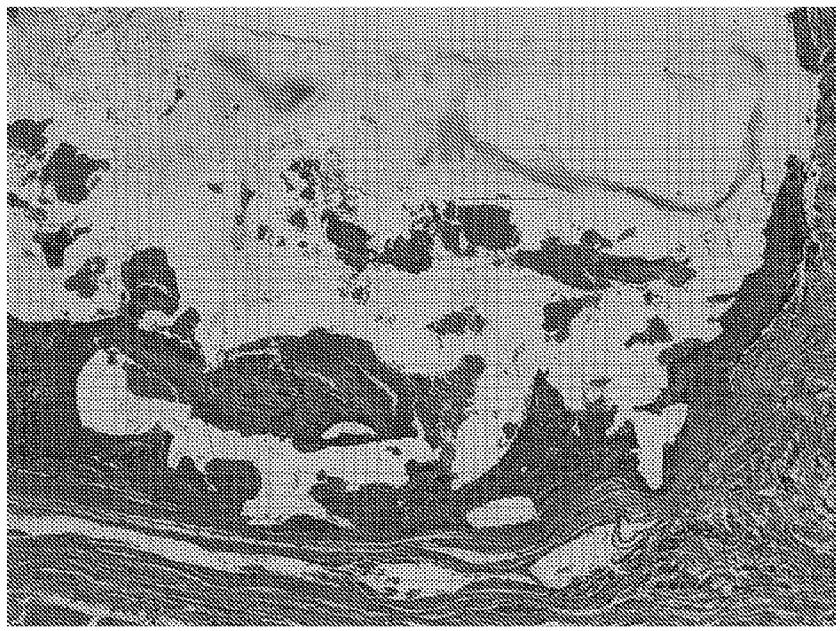
FIG. 4 illustrates an implant without sufficient pore size to allow substantial tissue ingrowth. Rather only a very fine layer of ingrowth is achieved.

In a further example, FIG. 4 illustrates a multilayer porous implant with large pores and small interconnections which are not abundant enough to allow substantial tissue ingrowth into the pores. A slight motion can disrupt the bridges formed between the implant and the tissue and causes bleeding via the broken blood vessels. Bleeding can be observed through the presence of erythrocytes (red blood cells), in the tissues. It has been observed that a 5 or 6 fold increase in capsule thickness results when such non-optimally interconnected foams are implanted. This increase in capsule thickness is likely a result of the continuous irritation and resulting inflammation that is present at the implantation site.

Figure 5:
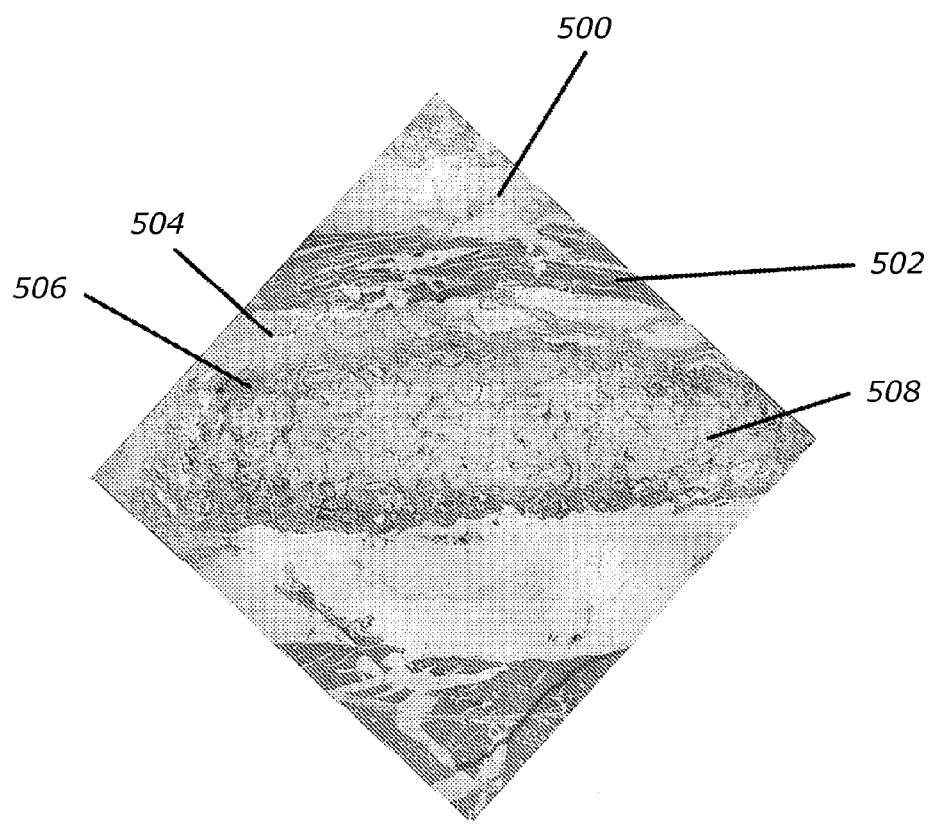
FIG. 5 illustrates an implanted polyurethane foam.

A typical polyurethane foam implant is illustrated under low magnification in FIG. 5. From top to bottom is disrupted dermis 500 (this is an artifact of histology) followed by the panniculus carnosus muscle 502, followed by loose connective tissue 504 (fascia), followed by an increase in connective tissue 506 density, followed by polyurethane implant 508. Polyurethane is also present in the area of connective tissue 506, as connective tissue is ingrown into the polyurethane.

The implant is fully infiltrated with loose connective tissue. However, the observed increase in tissue density at the implant-fascia interface can be a potential pathological response, e.g. a capsule, which can be prone to contracture. The tissue density is highly disorganized and the ingrowth may make the implant perform better than the smooth or possibly standard textured materials with respect to capsule formation, but at later stages, as a result of the biodegradable nature of the polyurethane foam, a smooth implant remains and the tissue can potentially revert to a pathological state. The other disadvantage of this approach is the fact that polyurethane eventually degrades, releasing a potentially carcinogenic diamines. The other disadvantage is the fact that degradation of the foam eventually leads to the formation of a predominantly smooth implant surface and the contracture rates increase.

Figure 6:
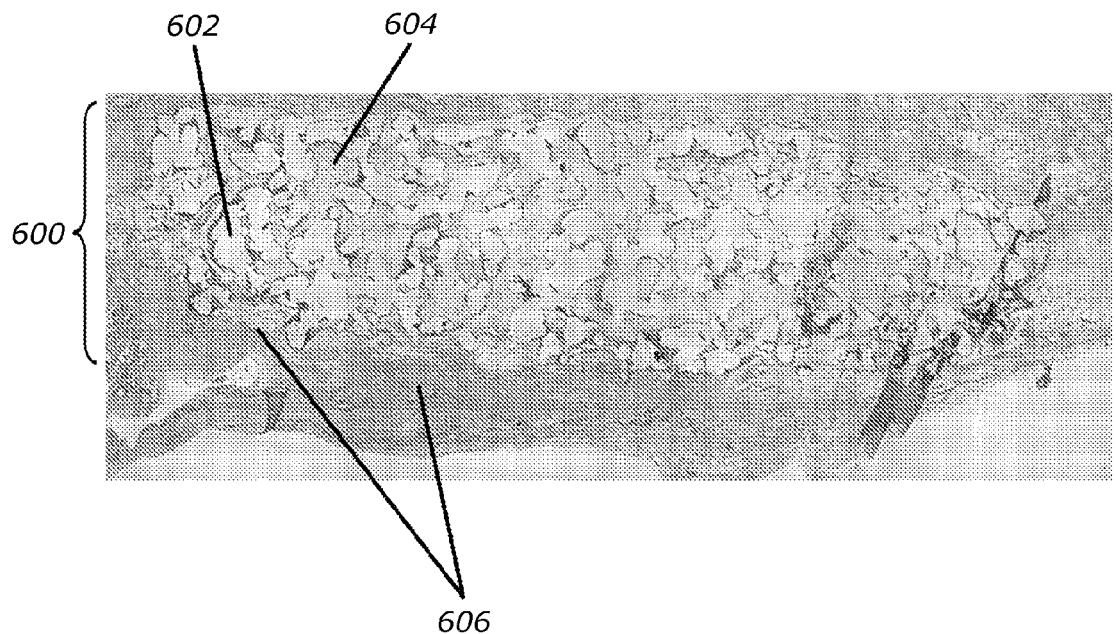
FIG. 6 illustrates an open celled foam implant produced according to the present description without capsule formation.

An open celled foam coated implant 600 made according to the present description is illustrated in FIG. 6. The open celled foam is composition F42 from Table 1. As can be seen in FIG. 6, implant 600 includes interconnected silicone 602 and pores 604 associated with the open celled foam. Also, there is an increase in tissue density around the implant, including loose disorganized fascia 606, and there is a tissue density decrease for the tissue that has ingrown into the implant. No pathological capsule is present. As such, there is nothing present that could undergo a contracture similar to that seen on implants known in the art. The advantages of the present open celled foams over polyurethane coated implants include, for example, their non-degradability, their ability to not generate harmful materials because of degradation and the absence of a tissue density increase, e.g. capsule, around the biomaterial.

Figure 7:
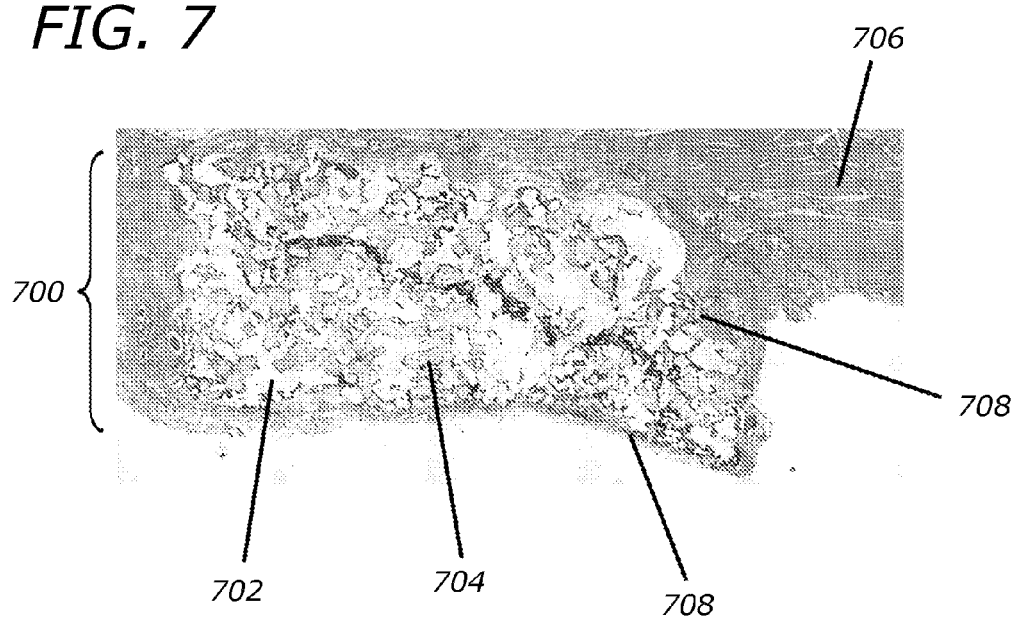
FIG. 7 illustrates another open celled silicone foam implant produced according to the present description without capsule formation.

Another example open celled foam coated implant 700 made according to the present description is illustrated in FIG. 7. The open celled foam is composition F35 from Table 1. As can be seen in FIG. 7, implant 700 includes interconnected silicone 702 and pores 704 associated with the open celled foam. Adjacent panniculus carnosus muscle 706 can be seen. Also, there is an increase in tissue density around the implant, including loose disorganized fascia 708. There is a difference in density/porosity of this composition when compared to that illustrated in FIG. 6, however, there is no capsule formation or visually quantifiable increase in collagenous tissue density towards the implant/tissue interface.

Example 6

Qualitative Studies

Figure 8:
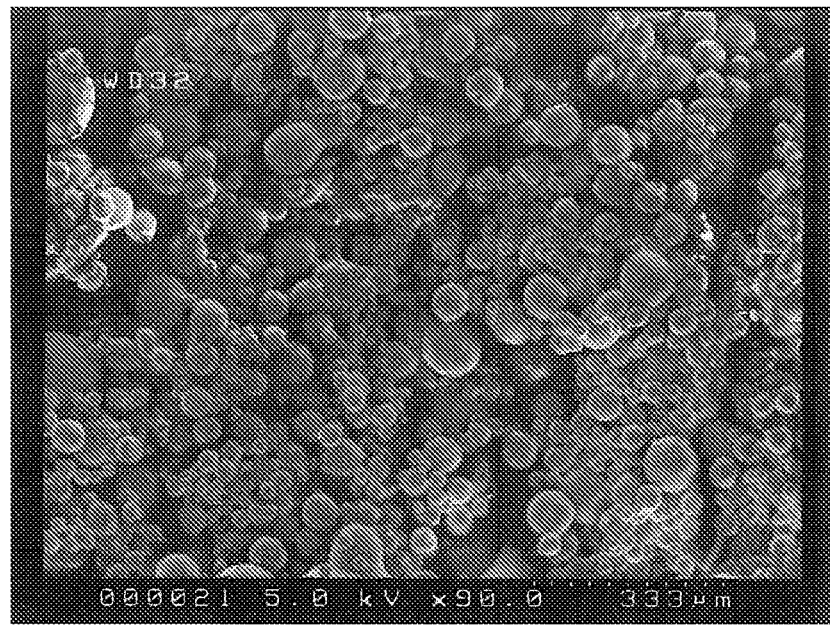
FIG. 8 illustrates a magnified image of open celled foam formulation F30 from Table 1.
Figure 9:
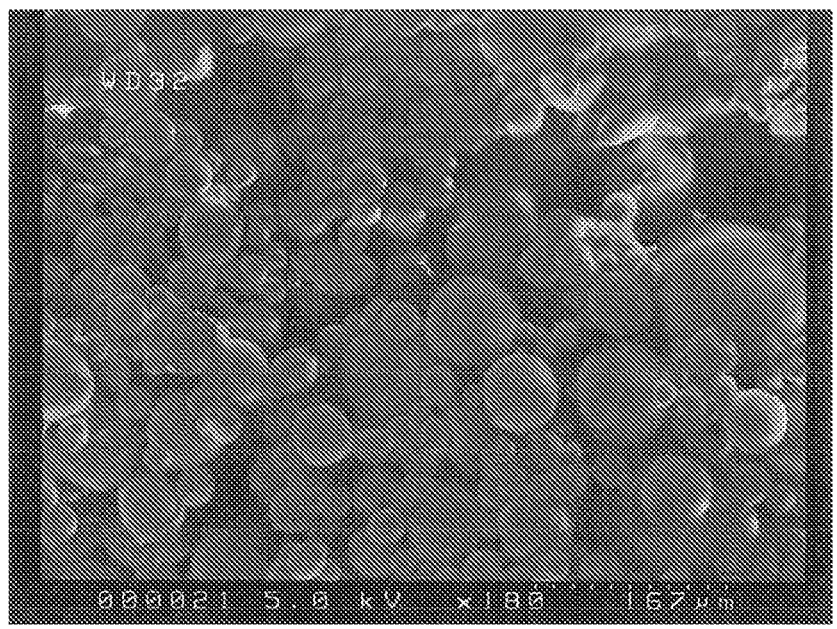
FIG. 9 illustrates a second magnified image of open celled foam formulation F30 from Table 1.
Figure 10:
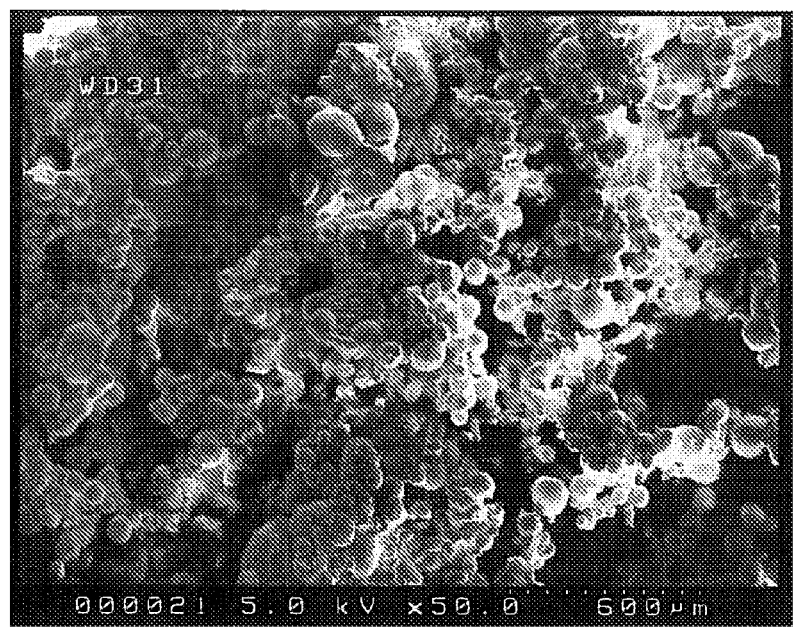
FIG. 10 illustrates a magnified image of open celled foam formulation F31 from Table 1.
Figure 11:
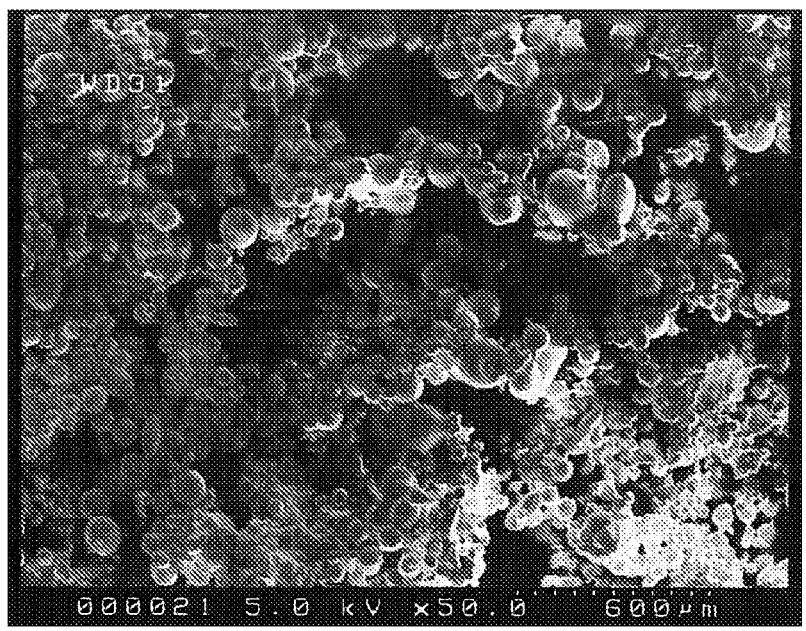
FIG. 11 illustrates a magnified image of open celled foam formulation F31 from Table 1.
Figure 12:
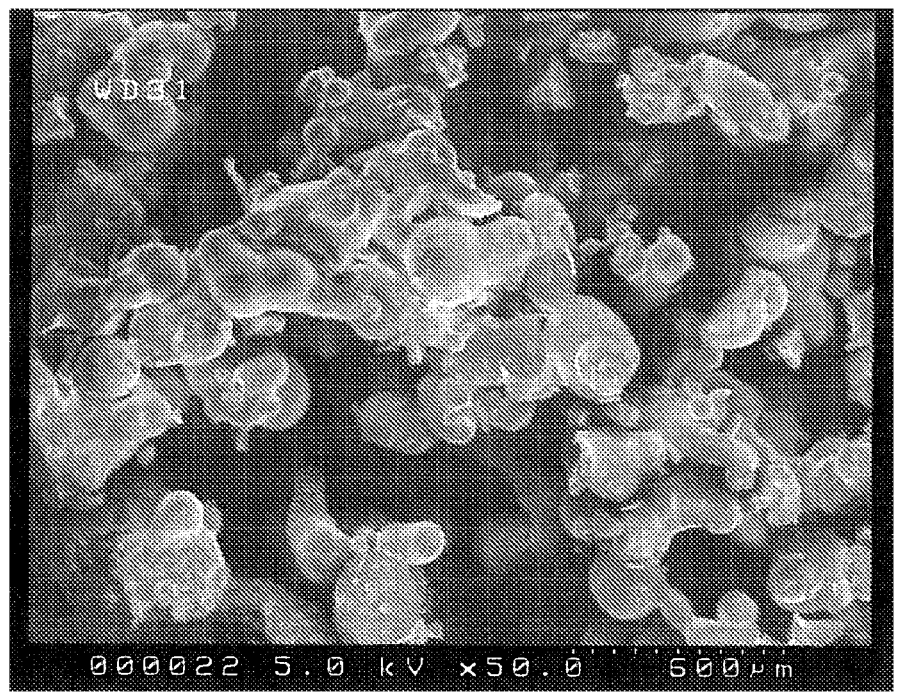
FIG. 12 illustrates a magnified image of a cross-sectional view of open celled foam formulation F35 from Table 1.
Figure 13:
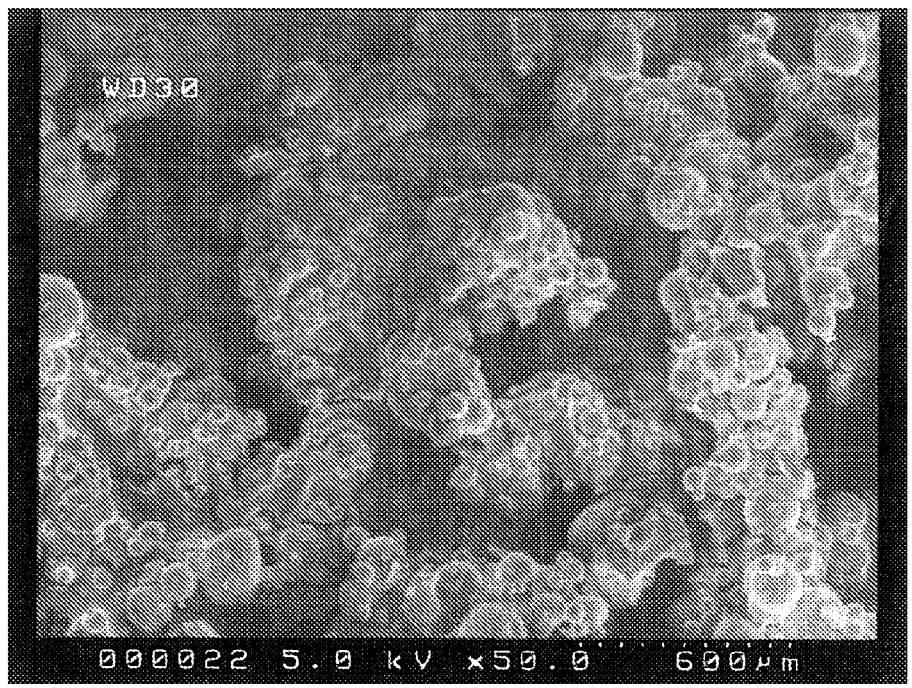
FIG. 13 illustrates a magnified image of a bottom view of open celled foam formulation F35 from Table 1.
Figure 14:
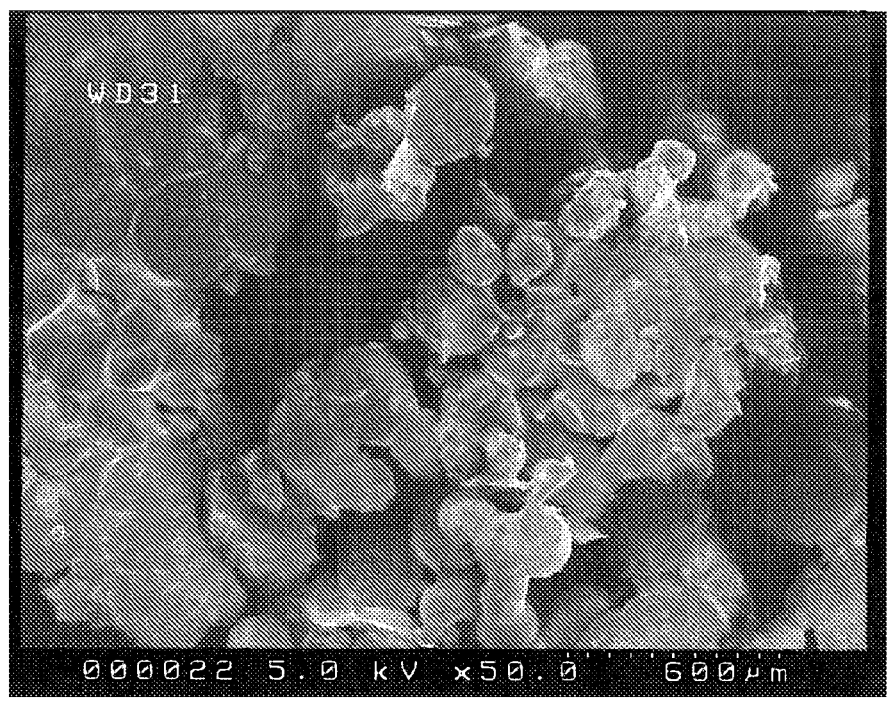
FIG. 14 illustrates a magnified image of a top view of open celled foam formulation F35 from Table 1.
Figure 15:
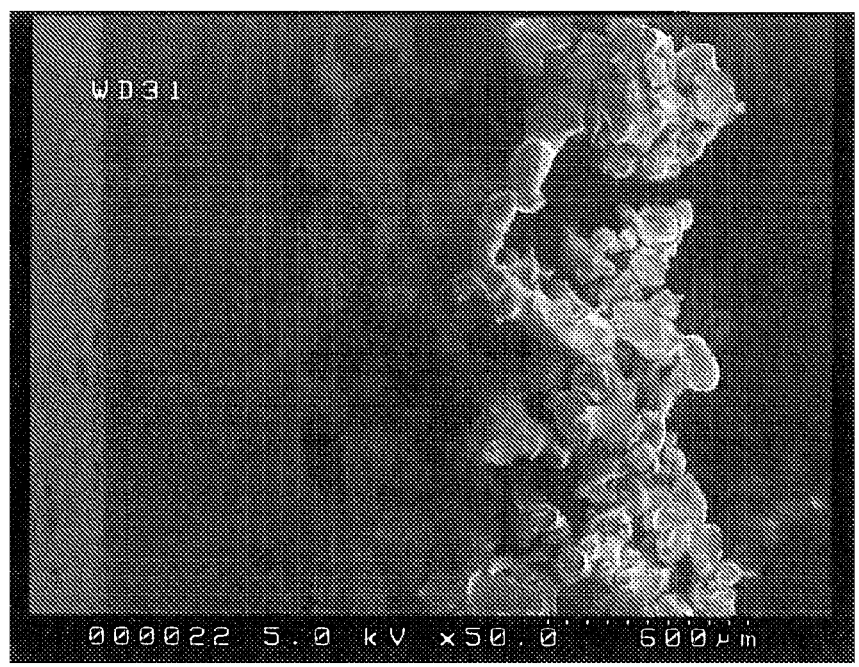
FIG. 15 illustrates a magnified image of open celled foam formulation F42 from Table 1 attached to a solid RTV silicone backing.
Figure 16:
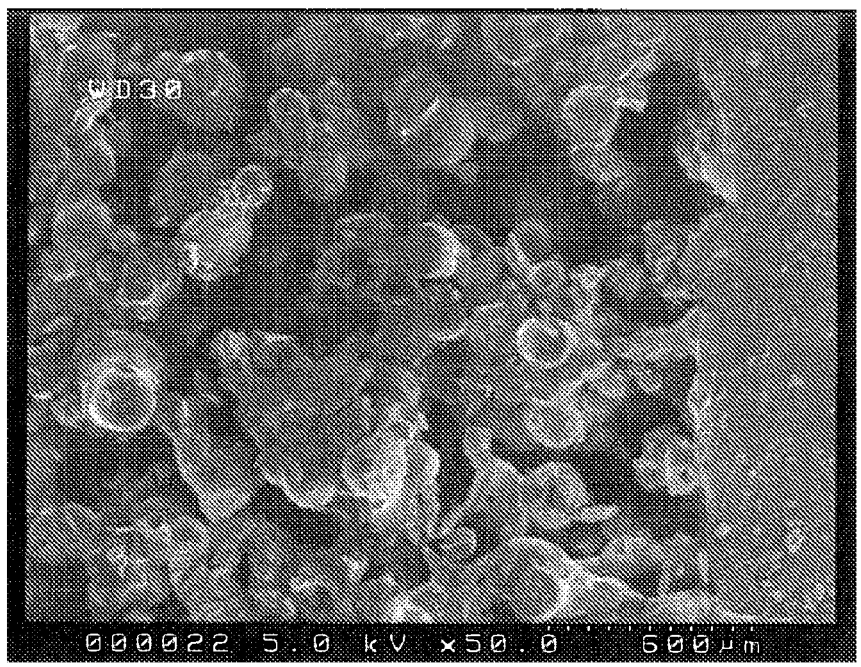
FIG. 16 illustrates a magnified image of open celled foam formulation F36 from Table 1 attached to a solid RTV silicone backing.
Figure 17:
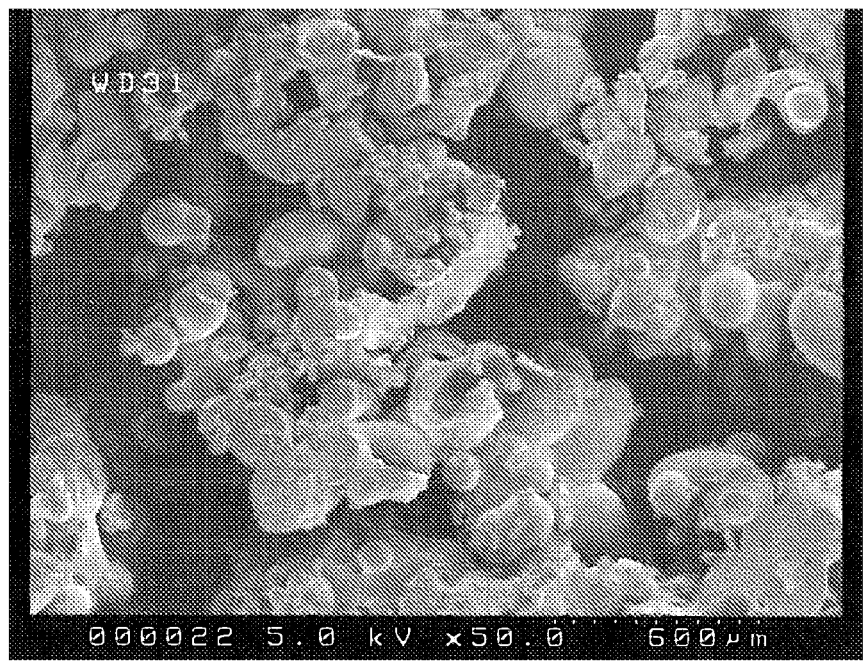
FIG. 17 illustrates a magnified image of a cross-sectional view of open celled foam formulation F36 from Table 1.
Figure 18:
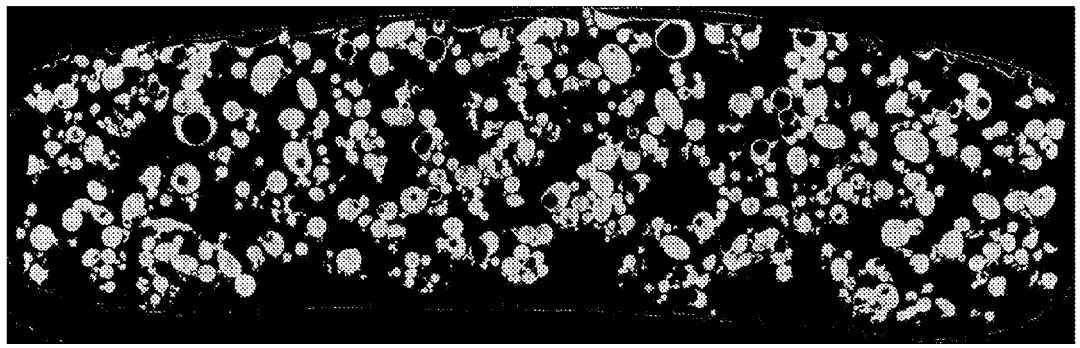
FIG. 18 illustrates a magnified image of an open celled foam showing actual void space.
Figure 19:
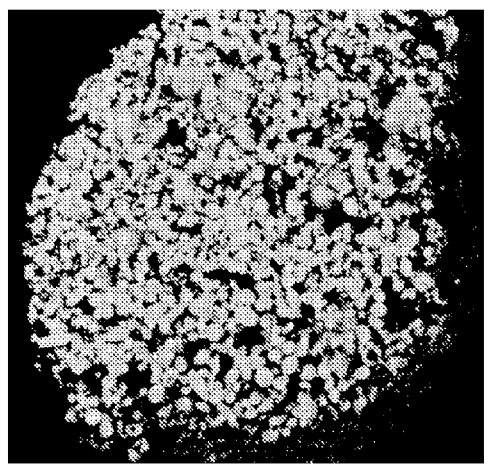
FIG. 19 illustrates a magnified image of another open celled foam showing actual void space.
Figure 20:
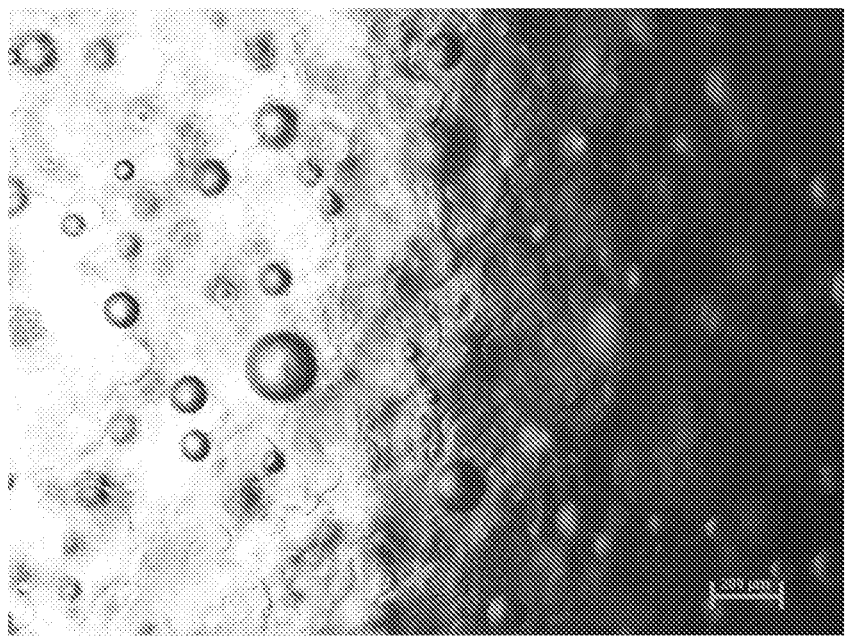
FIG. 20 illustrates a magnified image of an emulsion showing the size distribution of microspheres present therein.
Figure 21:
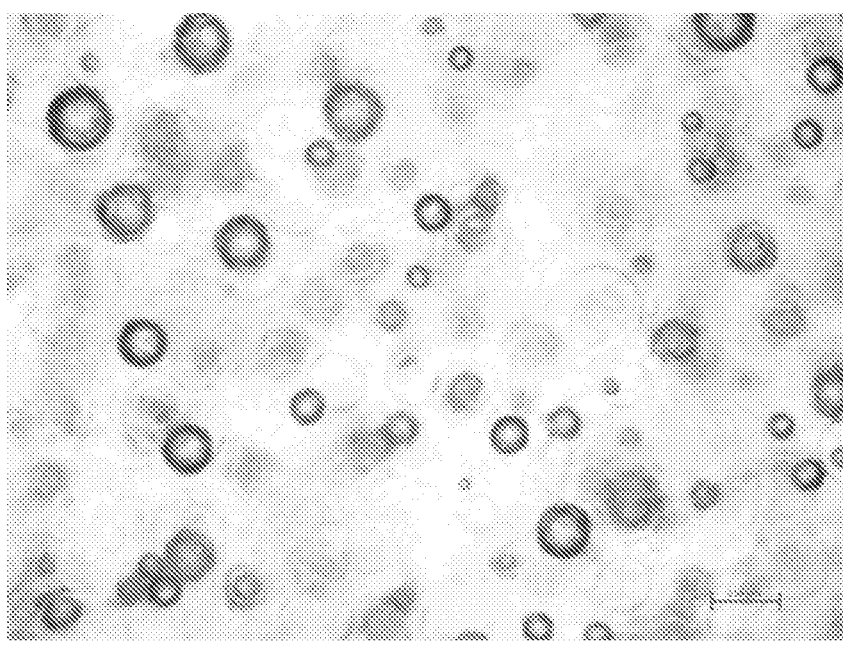
FIG. 21 illustrates a magnified image of another emulsion showing the size distribution of microspheres present therein.

Various open celled foams were visualized under a scanning electron microscope (SEM). FIGS. 8 and 9 are SEM images of formulation F30 from Table 1 which illustrate the interconnected network or matrix of microspheres. The void space of the foam is clearly visible. FIGS. 10 and 11 are SEM images of formulation F31 form Table 1 which illustrate the interconnected network or matrix of microspheres. Again, the void space of the foam is clearly visible. FIGS. 12, 13 and 14 are SEM images (middle, bottom and top respectively) of formulation F35 form Table 1 which illustrate the interconnected network or matrix of microspheres. The microspheres here are a bit less defined, but a matrix of interconnected spheres is still formed. Again, the void space of the foam is clearly visible. FIG. 15 is a SEM image of formulation F42 form Table 1 which illustrates the interconnected network or matrix of microspheres attached to a solid RTV silicone backing. Again, the void space of the foam is clearly visible. FIGS. 16 and 17 are SEM images of formulation F36 form Table 1 which illustrate the interconnected network or matrix of microspheres. FIG. 16 illustrates formulation F36 on a solid RTV silicone backing and FIG. 17 is a cross sectional view. Again, the void space of the foam is clearly visible in both figures.

Example 7

Lamination of a Soft Tissue Implant

This Example describes laminating open celled foams of the present description onto a finished smooth implant. The present process requires the use of a two piece cavity. A 40% dispersion of MED-1037 adhesive silicone by weight in xylene is used as the adhesive between the implant and the foam sheets, for example F31 from Example 2. First, the foam sheet is coated with a thin layer of 40% MED-1037 adhesive silicone and then placed in the bottom cavity. The smooth implant is then placed on top of the foam sheet in the bottom cavity. The second foam sheet is coated with a thin layer of 40% MED-1037 adhesive silicone and applied on top of the smooth implant. The top piece of the cavity is then fixed in place pressing the two foam sheets together creating a uniform interface. The silicone adhesive is allowed to cure and then the excess foam is cut off creating a uniform seam around the implant.

Example 8

Lamination of a Soft Tissue Implant on a Mandrel

Another process involves laminating the foam, for example F31 from Example 2, onto a smooth implant still on a mandrel. In this process a 40% dispersion of MED-1037 adhesive silicone by weight in xylene is used as the adhesive between the implant and the foam sheets. The first foam sheet is coated with a thin layer of 40% MED-1037 adhesive silicone and then draped over the smooth implant on the mandrel in such a way that there are no wrinkles on the top surface. After this has cured, another coating of 40% MED 1037 adhesive silicone is applied and the foam is stretched up to cover part of the back of the implant. The smooth implant is then taken off the mandrel and the excess foam is removed. A smaller circle is cut out of a foam sheet to fit the back of the implant. A thin layer of 40% MED-1037 adhesive silicone is applied to the small circle of foam and the circle is attached and allowed to cure.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A soft tissue implant comprising:
   a textured coating on at least a portion of said implant, said coating comprising a matrix of interconnected spheres having a physical void space of about 50% to about 70%, said spheres comprising substantially pure silicone.

2. The soft tissue implant of claim 1 wherein said matrix of interconnected spheres has a theoretical void space of about 50% to about 99%.

3. The soft tissue implant of claim 2 wherein said theoretical void space is between about 60% and about 88%.

4. The soft tissue implant of claim 1 wherein said spheres have a diameter of between about 25 μm and about 200 μm.

5. A soft tissue implant comprising:
   a textured coating on at least a portion of said implant, said coating comprising a matrix of interconnected spheres having a theoretical void space of between about 60% and about 88%, said spheres comprising substantially pure silicone.

6. A breast implant comprising:
   a fillable elastomeric shell; and
   a textured coating on at least a portion of said shell, said coating comprising a matrix of interconnected spheres having a having a physical void space of about 50% to about 70%, said spheres comprising substantially pure silicone.

7. The soft tissue implant of claim 6 wherein said spheres have a diameter of between about 25 μm and about 200 μm.

8. A breast implant comprising:
   a fillable elastomeric shell; and
   a textured coating on at least a portion of said shell, said coating comprising a matrix of interconnected spheres having a theoretical void space of between about 60% and about 88%, said spheres comprising substantially pure silicone.

9. The soft tissue implant of claim 8 wherein said spheres have a diameter of between about 25 μm and about 200 μm.

* * * * *

UNITED STATES PATENT AND TRADEMARK OFFICE
CERTIFICATE OF CORRECTION

PATENT NO. : 8,487,012 B2  
APPLICATION NO. : 13/012991  
DATED : July 16, 2013  
INVENTOR(S) : Goraltchouk et al.

It is certified that error appears in the above-identified patent and that said Letters Patent is hereby corrected as shown below:

In the Specification

In column 2, line 52-54, delete "disposed in the hub, further prevents detachment of the hub from the syringe distal end during ejection of the viscous fluid".

In the Claims

In column 16, line 35, in claim 7, delete "soft tissue" and insert therefor --breast--.

In column 16, line 44, in claim 9, delete "soft tissue" and insert therefor --breast--.

Signed and Sealed this
Twenty-eighth Day of April, 2015

Michelle K. Lee
*Director of the United States Patent and Trademark Office*